(12) United States Patent
Pratt et al.

(10) Patent No.: US 10,413,448 B2
(45) Date of Patent: *Sep. 17, 2019

(54) MEDICAL DRESSINGS, SYSTEMS, AND METHODS WITH THERMALLY-ENHANCED VAPOR TRANSMISSION

(71) Applicant: KCI Licensing, Inc., San Antonio, TX (US)

(72) Inventors: Benjamin Andrew Pratt, Poole (GB); Christopher Brian Locke, Bournemouth (GB); Richard Daniel John Coulthard, Verwood (GB); Timothy Mark Robinson, Basingstoke (GB)

(73) Assignee: KCI Licensing, Inc., San Antonio, TX (US)

( * ) Notice: Subject to any disclaimer, the term of this patent is extended or adjusted under 35 U.S.C. 154(b) by 493 days.

This patent is subject to a terminal disclaimer.

(21) Appl. No.: 14/960,058

(22) Filed: Dec. 4, 2015

(65) Prior Publication Data
US 2016/0151207 A1 Jun. 2, 2016

Related U.S. Application Data

(63) Continuation of application No. 13/678,492, filed on Nov. 15, 2012, now Pat. No. 9,233,028.
(Continued)

(51) Int. Cl.
A61F 13/00 (2006.01)
A61M 1/00 (2006.01)

(52) U.S. Cl.
CPC .. *A61F 13/00034* (2013.01); *A61F 13/00012* (2013.01); *A61F 13/00017* (2013.01);
(Continued)

(58) Field of Classification Search
CPC .......... A61F 13/00068; A61F 2013/002; A61F 2013/191
(Continued)

(56) References Cited

U.S. PATENT DOCUMENTS 1,355,846 A 10/1920 Rannells
2,547,758 A 4/1951 Kelling
(Continued)

FOREIGN PATENT DOCUMENTS

AU 550575 B2 3/1986
AU 745271 B2 3/2002
(Continued)

OTHER PUBLICATIONS

Thermal Conductivity of Common Materials and Gases, https://www.engineeringtoolbox.com/thermal-conductivity-d_429.html, printed Jan. 5, 2019.*
(Continued)

*Primary Examiner* — Susan S Su

(57) ABSTRACT

Wounds dressings, systems, and methods are presented that involve using a patient's body heat to enhance liquid removal from the wound dressing through a high-moisture-vapor-transmission-rate drape. Additional heat sources or devices, such as nano-antennas or electrical heating elements, may be added or used separately to enhance the removal liquid from the wound dressing. Other dressings, systems, and methods are presented herein.

35 Claims, 10 Drawing Sheets

Related U.S. Application Data

(60) Provisional application No. 61/560,090, filed on Nov. 15, 2011.

(52) U.S. Cl.
CPC .. *A61F 13/00063* (2013.01); *A61F 13/00068* (2013.01); *A61M 1/009* (2014.02); *A61F 2013/002* (2013.01); *A61F 2013/00212* (2013.01); *A61M 2205/3613* (2013.01)

(58) Field of Classification Search
USPC ............. 604/304, 313–316, 540, 543
See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Piass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,071,304 A | 6/2000 | Augustine et al. |
| 6,110,197 A | 8/2000 | Augustine et al. |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,613,953 B1 | 9/2003 | Altura |
| 6,814,079 B2 | 11/2004 | Heaton et al. |
| 7,048,976 B2 * | 5/2006 | Caceres ............... A41D 20/005 126/204 |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,398,614 B2 | 3/2013 | Blott et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,672,903 B2 * | 3/2014 | Hunt .................. A61M 1/0088 602/2 |
| 8,679,081 B2 | 3/2014 | Heagle et al. |
| 8,834,451 B2 | 9/2014 | Blott et al. |
| 8,853,603 B2 | 10/2014 | Sheehan |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2004/0030276 A1 | 2/2004 | Flick |
| 2004/0030304 A1 * | 2/2004 | Hunt .................. A61M 1/0088 604/317 |
| 2004/0267299 A1 * | 12/2004 | Kuriger ............. A61B 5/15186 606/181 |
| 2005/0240151 A1 * | 10/2005 | Hansmann ......... A61B 17/2202 604/113 |
| 2006/0020235 A1 | 1/2006 | Siniaguine |
| 2006/0155260 A1 | 7/2006 | Blott et al. |

(56) References Cited

U.S. PATENT DOCUMENTS

| | | | |
|---|---|---|---|
| 2008/0004559 A1* | 1/2008 | Riesinger | A61F 13/00012 602/46 |
| 2008/0167594 A1 | 7/2008 | Siniaguine | |
| 2008/0306456 A1* | 12/2008 | Riesinger | A61F 13/0203 604/316 |
| 2008/0312572 A1 | 12/2008 | Riesinger | |
| 2009/0099519 A1 | 4/2009 | Kaplan | |
| 2009/0299342 A1 | 12/2009 | Cavanaugh, II et al. | |
| 2010/0030171 A1 | 2/2010 | Canada et al. | |
| 2010/0262090 A1 | 10/2010 | Riesinger | |
| 2010/0312200 A1* | 12/2010 | Ferguson | A61F 7/007 604/290 |
| 2010/0324516 A1* | 12/2010 | Braga | A61F 13/00 604/378 |
| 2011/0040289 A1* | 2/2011 | Canada | A01N 59/16 604/543 |
| 2011/0257572 A1* | 10/2011 | Locke | A61F 13/02 602/46 |
| 2012/0238971 A1 | 9/2012 | Spinelli et al. | |
| 2013/0165821 A1* | 6/2013 | Freedman | A61F 13/00063 601/2 |
| 2014/0163491 A1 | 6/2014 | Schuessler et al. | |
| 2015/0080788 A1 | 3/2015 | Blott et al. | |
| 2016/0184595 A1* | 6/2016 | Hossainy | A61N 1/3756 604/288.04 |

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |
| WO | 2007070697 A2 | 6/2007 |
| WO | 2011130570 A1 | 10/2011 |
| WO | 2012019147 A1 | 2/2012 |

OTHER PUBLICATIONS

European Search Report for corresponding application 12794613.5, dated Sep. 4, 2017.

Australian Patent Examination No. 1 corresponding to AU2012340381 dated Jul. 13, 2016.

Louis C. Argenta, MD and Michael J. Morykwas, PHD; Vacuum-Assisted Closure: A New Method for Wound Cotrol and Treatment; Clinical Experience; Annals of Plastic Surgery.

Susan Mendez-Eatmen, RN; "When wounds Won't Heal" RN Jan. 1998, vol. 61 (1); Medical Economics Company, Inc., Montvale, NJ, USA; pp. 20-24.

James H. Blackburn II, MD et al.; Negative-Pressure Dressings as a Bolster for Skin Grafts; Annals of Plastic Surgery, vol. 40, No. 5, May 1998, pp. 453-457; Lippincott Williams & Wilkins, Inc., Philadelphia, PA, USA.

John Masters; "Reliable, Inexpensive and Simple Suction Dressings"; Letter to the Editor, British Journal of Plastic Surgery, 198, vol. 51 (3), p. 267; Elsevier Science/The British Association of Plastic Surgeons, UK.

S.E, Greer, et al. "The Use of Subatmospheric Pressure Dressing Therapy to Close Lymphocutaneous Fistulas of the Groin" British Journal of Plastic Surgery (2000), 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; dated Nov. 23, 1995.

PCT International Search Report for PCT International Application PCT/GB98/02713; dated Jan. 8, 1999.

PCT Written Opinion; PCT International Application PCT/GB98/02713; dated Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; dated Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 an 6 page English translation therof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

Yusupov. YU.N., et al; "Active Wound Drainage", Vestnki Khirurgi, vol. 138, Issue 4, 1987, and 7 page English translation thereof.

Davydov, Yu.A., et al; "Bacteriological and Cytological Assessment of Vacuum Therapy for Purulent Wounds"; Vestnik Khirugi, Oct. 1988, pp. 48-52, and 8 page English translation thereof.

Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, pp. 2.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., No. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al: "A Dressing System Providing Fluid Supply and Suction Drainage Used for Continuous of Intermittent Irrigation", Annals of Plastic Surgery, vol. 17, No. 2, Aug. 1986, pp. 125-133.

N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkav et al. (Chuvashia State University, Cheboksary, U.S.S.R. 1986); pp. 94-96 (copy and translation).

K.F. Jeter, T.E. Tintle, and M. Chariker, "Managing Draining Wounds and Fistulae: New and Established Methods," Chronic

(56) References Cited

OTHER PUBLICATIONS

Wound Care, edited by D. Krasner (Health Management Publications, Inc., King of Prussia, PA 1990), pp. 240-246.

G. Živadinovi?, V. ?uki?, Ž. Maksimovi?, ?. Radak, and P. Peška , "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, An Improved Sump Drain-Irrigation Device of Simple Construction, Archives of Surgery 105 (1972) pp. 511-513.

M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).

C.E. Tennants, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.a. Bagautdinov, "Vacuum and Vacuum-Sorption Treatment of Open Septic Wounds," in II All-Union Conference on Wounds and Wound Infections; Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians; Jul. 2007.

International Search Report and Written Opinion for corresponding PCT/US2012/065335, dated Feb. 4, 2013.

Iranian Journal of Polymer Science & Technology. vol. 1 , No. 1. Jan. 1992. Internal Heat Generation and Fatigue Life Behavior of Polyurethane Elastomer Based on Trans 4 , 4—Cycloheaxane Diisocyanate.

\* cited by examiner

MEDICAL DRESSINGS, SYSTEMS, AND METHODS WITH THERMALLY-ENHANCED VAPOR TRANSMISSION

RELATED APPLICATIONS

This application is a continuation of U.S. patent application Ser. No. 13/678,492, filed Nov. 15, 2012, which claims the benefit, under 35 USC § 119(e), of the filing of U.S. Provisional Patent Application Ser. No. 61/560,090, entitled "Medical Dressing, Systems, and Methods with Thermally Enhanced Vapor Transmission," by Pratt et al., filed Nov. 15, 2011, which is incorporated herein by reference for all purposes.

FIELD

The present disclosure relates generally to medical treatment systems for treating wounds that produce liquids, such as exudate, and more particularly, but not by way of limitation, to medical dressings, systems, and methods with thermally-enhanced vapor transmission.

BACKGROUND

Caring for wounds is important in the healing process. Wounds often produce considerable liquids, e.g., exudate. Medical dressings are often used in wound care to address the production of liquids from the wound. If not properly addressed, liquids at the wound can lead to infection or maceration of the periwound area. As used throughout this document, "or" does not require mutual exclusivity. Wound dressings may be used alone or as an aspect of applying reduced pressure to a tissue site.

SUMMARY

According to an illustrative embodiment, a wound dressing includes a high-moisture-vapor-transmission-rate drape having a first side and a second, patient-facing side and includes a thermally-conductive, vapor-permeable member. The thermally-conductive, vapor-permeable member includes a drape-interface member having a first side and a second, patient-facing side, wherein the first side of the drape-interface member is proximate the second, patient-facing side of the high-moisture-vapor-transmission-rate drape; a patient-interface member having a first side and a second, patient-facing side, wherein the second, patient-facing side of the patient-interface member is proximate to the patient; and a coupling member that thermally couples the drape-interface member and the patient-interface member. The wound dressing further includes a liquid-processing member disposed between the drape-interface member and the patient-interface member, wherein the liquid-processing member is operable to at least temporarily retain liquids from the wound. The thermally-conductive, vapor-permeable member is operable to conduct body heat from the patient to the high-moisture-vapor-transmission-rate drape to enhance transmission of vapor through the high-moisture-vapor-transmission-rate drape. A number of additional elements may be added to further enhance transmission across the high-moisture-vapor-transmission-rate drape.

According to another illustrative embodiment, a method for treating a wound on a patient includes covering the wound with a wound dressing. The wound dressing includes a high-moisture-vapor-transmission-rate drape having a first side and a second, patient-facing side, a thermally-conductive, vapor-permeable member, and a liquid-processing member. The method also includes using the thermally-conductive, vapor-permeable member to conduct heat from the patient's body to the high-moisture-vapor-transmission-rate drape to enhance vapor transmission.

According to another illustrative embodiment, a method of manufacturing a wound dressing includes providing a thermally-conductive, vapor-permeable member. The thermally-conductive, vapor-permeable member includes a drape-interface member having a first side and a second, patient-facing side; a patient-interface member having a first side and a second, patient-facing side, wherein the second, patient-facing side of the patient-interface member is for placing proximate to the patient; and a coupling member thermally coupling the drape-interface member and the patient-interface member. The method also includes disposing a liquid-processing member between the drape-interface member and the patient-interface member, wherein the liquid-processing member is operable to at least temporarily retain liquids from the wound; and disposing a high-moisture-vapor-transmission-rate drape having a first side and a second, patient-facing side over the thermally-conductive, vapor-permeable member, wherein the first side of the drape-interface member is proximate the second, patient-facing side of the high-moisture-vapor-transmission-rate drape.

Other aspects, features, and advantages of the illustrative embodiments will become apparent with reference to the drawings and detailed description that follow.

DETAILED DESCRIPTION OF ILLUSTRATIVE EMBODIMENTS

In the following detailed description of illustrative, non-limiting embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is not to be taken in a limiting sense, and the scope of the illustrative embodiments are defined only by the appended claims.

The illustrative medical systems, dressings, and methods herein improve the fluid management of a wound. The illustrative medical systems, dressings, and methods thermally-enhance transmission of vapor across a sealing member to allow the system or dressing to process more liquid than otherwise possible.

Figure 1:
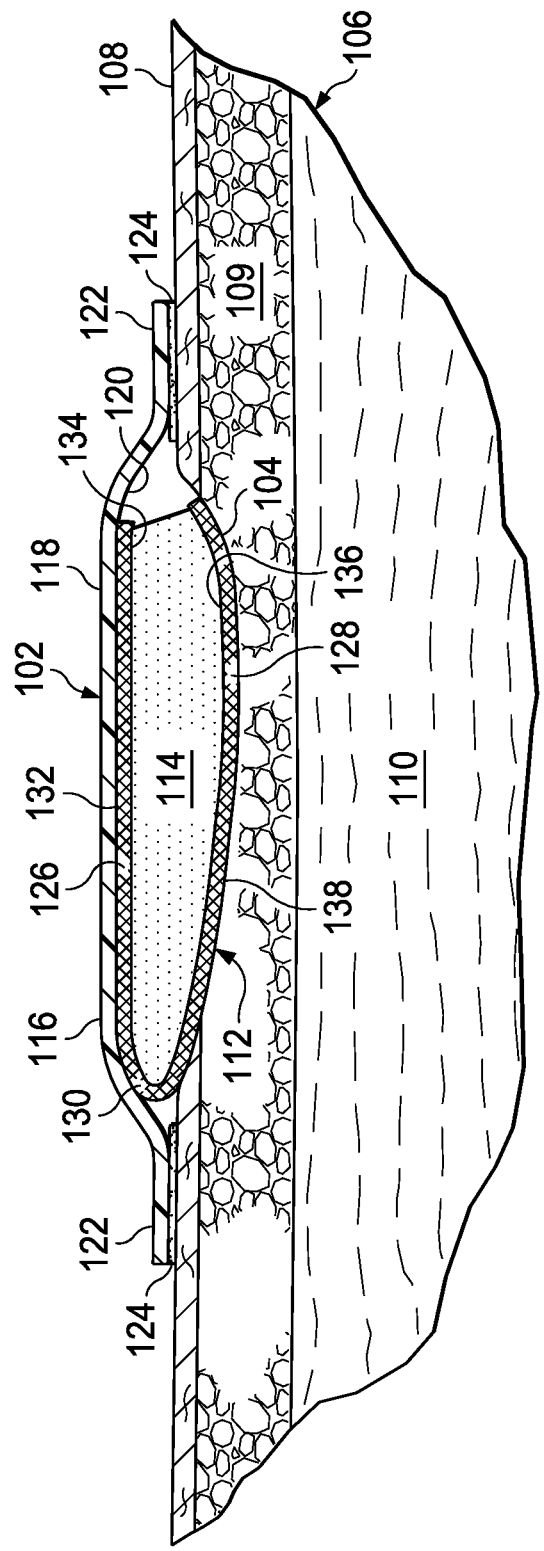
FIG. 1 is a cross section of an illustrative embodiment of a wound dressing on a patient's wound.
Figure 2:
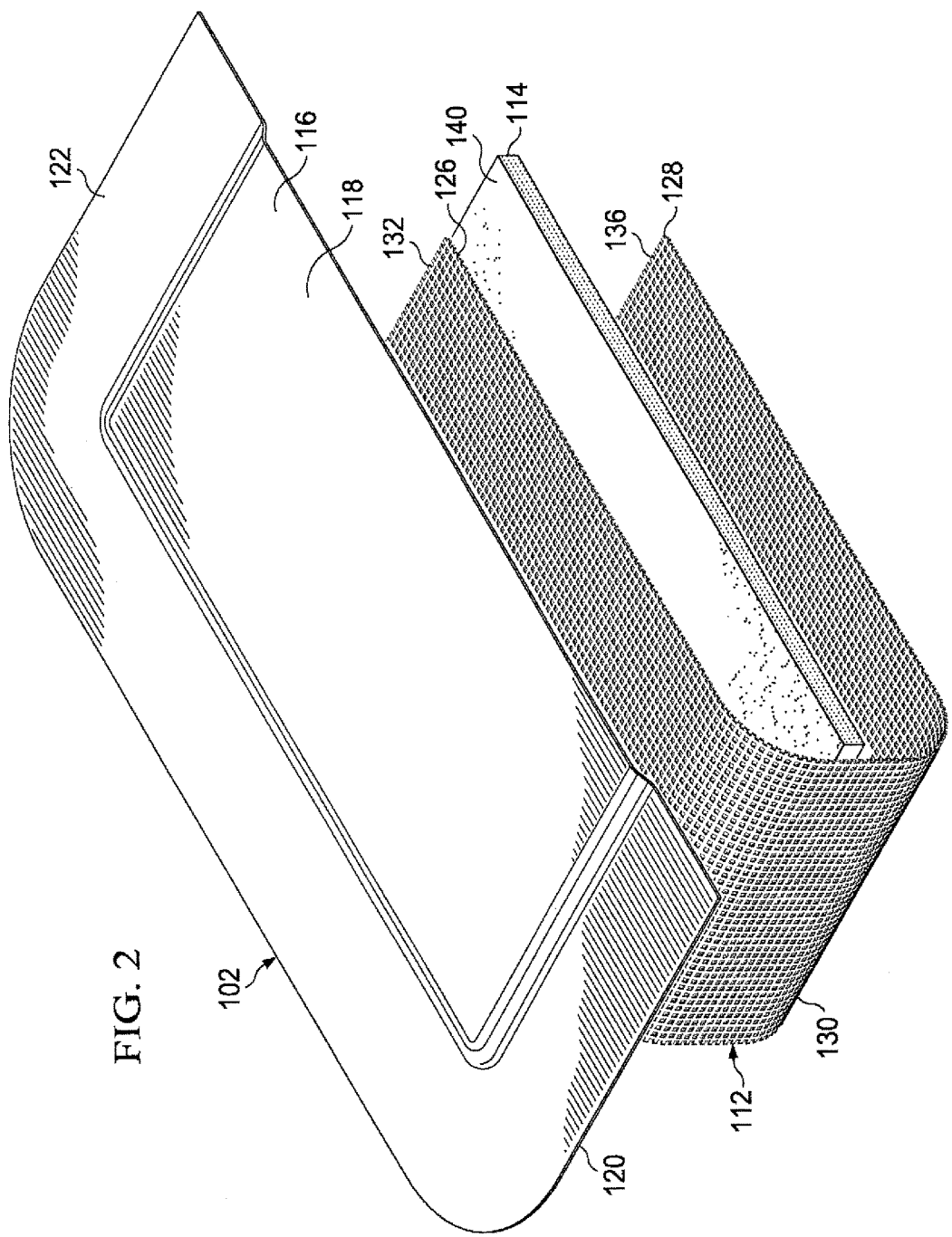
FIG. 2 is an exploded, perspective view, with a portion (an edge) shown in cross section, of an illustrative embodiment of a wound dressing.
Figure 3:
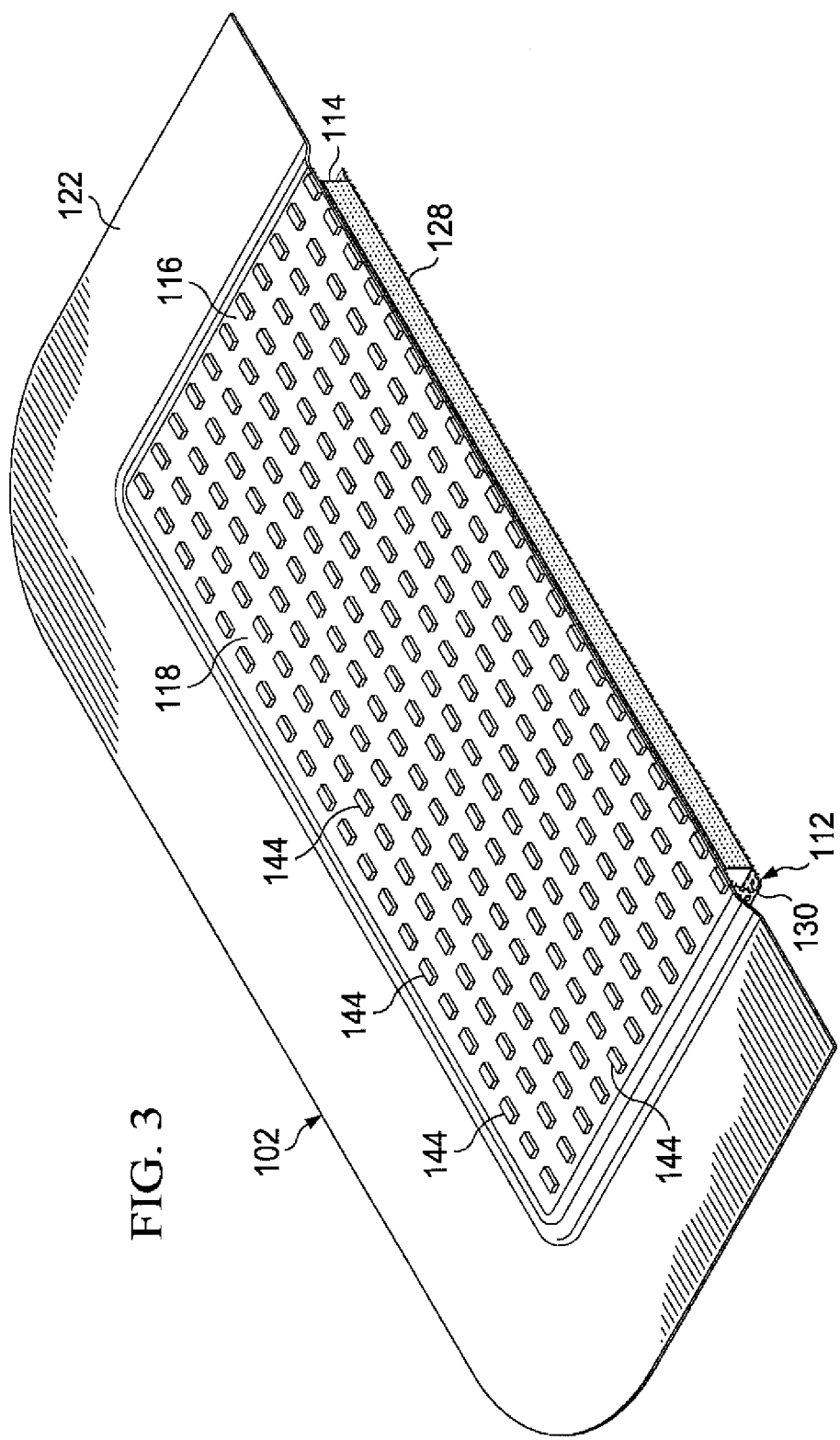
FIG. 3 is a perspective view, with a portion shown in cross section, of the wound dressing of FIG. 2 shown with a plurality nano-antennas.

Referring now primarily to FIGS. 1-4, an illustrative embodiment of a wound dressing 102 is presented. In FIG. 1, the wound dressing 102 is shown on a wound 104, or tissue site. The wound is through a patient's 106 epidermis 108, a dermis 109, and into subcutaneous tissue 110. The wound dressing 102 includes a thermally-conductive, vapor-permeable member 112 and a liquid-processing member 114. While referencing only "vapor" in its name, the thermally-conductive, vapor-permeable member 112 is operable to allow vapor and liquid to pass. The thermally-conductive, vapor-permeable member 112 and liquid-processing member 114 are covered by a high-moisture-vapor-transmission-rate drape 116 (high-MVTR drape). The thermally-conductive, vapor-permeable member 112 is operable to conduct body heat from the patient 106 at or near the wound 104 to the high-moisture-vapor-transmission-rate drape 116 to enhance transmission of vapor through the high-moisture-vapor-transmission-rate drape 116.

The heat captured by the thermally-conductive, vapor-permeable member 112 of the wound dressing 102 and delivered specifically to the high-moisture-vapor-transmission-rate drape 116 increases vapor transmission through the high-moisture-vapor-transmission-rate drape 116. As described further below, in addition to or separate from capturing body heat, other sources of internal and external heat may be utilized with the wound dressing 102 to increase vapor transmission through the high-moisture-vapor-transmission-rate drape 116.

Enhancing the vapor transmission through the wound dressing 102 maximizes the capacity of the wound dressing 102. The wound dressing 102 becomes operable to process more liquid over time than the wound dressing 102 can hold at one time. The wound dressing 102 effectually removes or manages liquid from the wound 104. The increased vapor transmission can be notable. For example, increasing the temperature from 20° C. to 30° C. or 40° C. may add orders of magnitude to the evaporation rate. In one illustrative, non-limiting example, a 1.3 fold increase in evaporation rate per degree was associated with each degree increase in Celsius (C) from 25° C. to 37° C. The increased evaporation rate in turn may greatly enhance the amount of liquid from the wound 104 that may be processed over time by the wound dressing 102.

The high-moisture-vapor-transmission-rate drape 116 has a first side 118 and a second, patient-facing side 120. "Moisture Vapor Transmission Rate" or "MVTR" represents the amount of moisture that can pass through a material in a given period of time. The high-moisture-vapor-transmission-rate drape 116 will typically have an MVTR greater than 300 g/24 hours/m$^2$ and more typically a value greater than or equal to 1000 g/24 hours/m$^2$. The high-moisture-vapor-transmission-rate drape 116 allows vapor to egress from the wound dressing 102 to the atmosphere. The high-moisture-vapor-transmission-rate drape 116 may comprise any of numerous materials, such as any of the following: hydrophilic polyurethane, cellulosics, hydrophilic polyamides, polyvinyl alcohol, polyvinyl pyrrolidone, hydrophilic acrylics, hydrophilic silicone elastomers, and copolymers of these. As one specific, illustrative, non-limiting embodiment, the high-moisture-vapor-transmission-rate drape 116 may be formed from a breathable cast matt polyurethane film sold under the name INSPIRE 2301 from Expopack Advanced Coatings of Wrexham, United Kingdom. That illustrative film has a MVTR (inverted cup technique) of 14400 g/m$^2$/24 hours. The high-moisture-vapor-transmission-rate drape 116 may have various thicknesses, such as 10 to 40 microns (μm), e.g., 15, 20, 25, 30, 35, 40 microns or any number in the stated range.

A peripheral edge 122 of the high-moisture-vapor-transmission-rate drape 116 has an attachment device 124 on the second, patient-facing side 120. The attachment device 124 secures or helps secure the high-moisture-vapor-transmission-rate drape 116 to the patient's intact skin at or near the wound 104. The attachment device 124 may be a medically-acceptable, pressure-sensitive adhesive; a double-sided drape tape; paste; hydrocolloid; hydro gel; or other sealing devices or elements.

The thermally-conductive, vapor-permeable member 112 functionally conducts heat from the patient 106 at or near the wound 104 to the high-moisture-vapor-transmission-rate drape 116 and allows or enhances vapor transmission through the thermally-conductive, vapor-permeable member 112. While the thermally-conductive, vapor-permeable member 112 may be formed as integral components, the thermally-conductive, vapor-permeable member 112 may nonetheless be viewed as comprising three portions or members: a drape-interface member 126, a patient-interface member 128, and a coupling member 130. The drape-interface member 126 has a first side 132 and a second, patient-facing side 134. The first side 132 of the drape-interface member 126 is proximate the second, patient-facing side 120 of the high-moisture-vapor-transmission-rate drape 116. The patient-interface member 128 has a first side 136 and a second, patient-facing side 138. The second, patient-facing side 138 of the patient-interface member 128 is proximate to the patient 106. The coupling member 130 thermally couples the drape-interface member 126 and the patient-interface member 128.

The thermally-conductive, vapor-permeable member 112 may be formed from any material that conducts thermal energy and allows liquid and vapor to transgress the material. For example, the thermally-conductive, vapor-permeable member 112 may comprise one or more of the following: woven or non-woven material, activated carbon material, porous foam, sintered polymer, carbon fiber material, woven metallic fibers, zinc oxide, or mesh fabric. The thermally-conductive, vapor-permeable member 112 is sized and configured to be flexible enough to conform to the shape of the wound 104.

Disposed between the drape-interface member 126 and the patient-interface member 128 is the liquid-processing member 114. The liquid-processing member 114 is operable to at least temporarily retain liquids from the wound 104. The liquid-processing member 114 has a first side 140 and a second, patient-facing side 142. The first side 140 is proximate the second, patient-facing side 134 of the drape-interface member 126. The second, patient-facing side 142 is proximate to the first side 136 of the patient-interface member 128.

The liquid-processing member 114 functions to retain, at least temporarily, liquids from the wound 104. The liquid-processing member 114 buffers liquids while waiting on evaporation or removal or may store a certain quantity of liquids for other reasons. The liquid-processing member 114 may be formed from one or more of the following: open-cell foam, non-woven material, a super-absorbent material, gel materials, absorbent clays or inorganic or polymer particulates, and nano particles.

In addition to or separate from capturing the patient's body heat and conducting the heat from at or near the wound 104 to the high-moisture-vapor-transmission-rate drape 116, thermal energy may be added to enhance evaporation from an internal heat source or external heat source. For example, heat from external air temperature, light, artificial radiation (infrared), hydro-activated chemicals, inductive materials, piezoelectric members, electric heating elements, or sonic heating (thermo-acoustic) may be used to enhance transmission of vapor through the high-moisture-vapor-transmission-rate drape 116.

Figure 4:
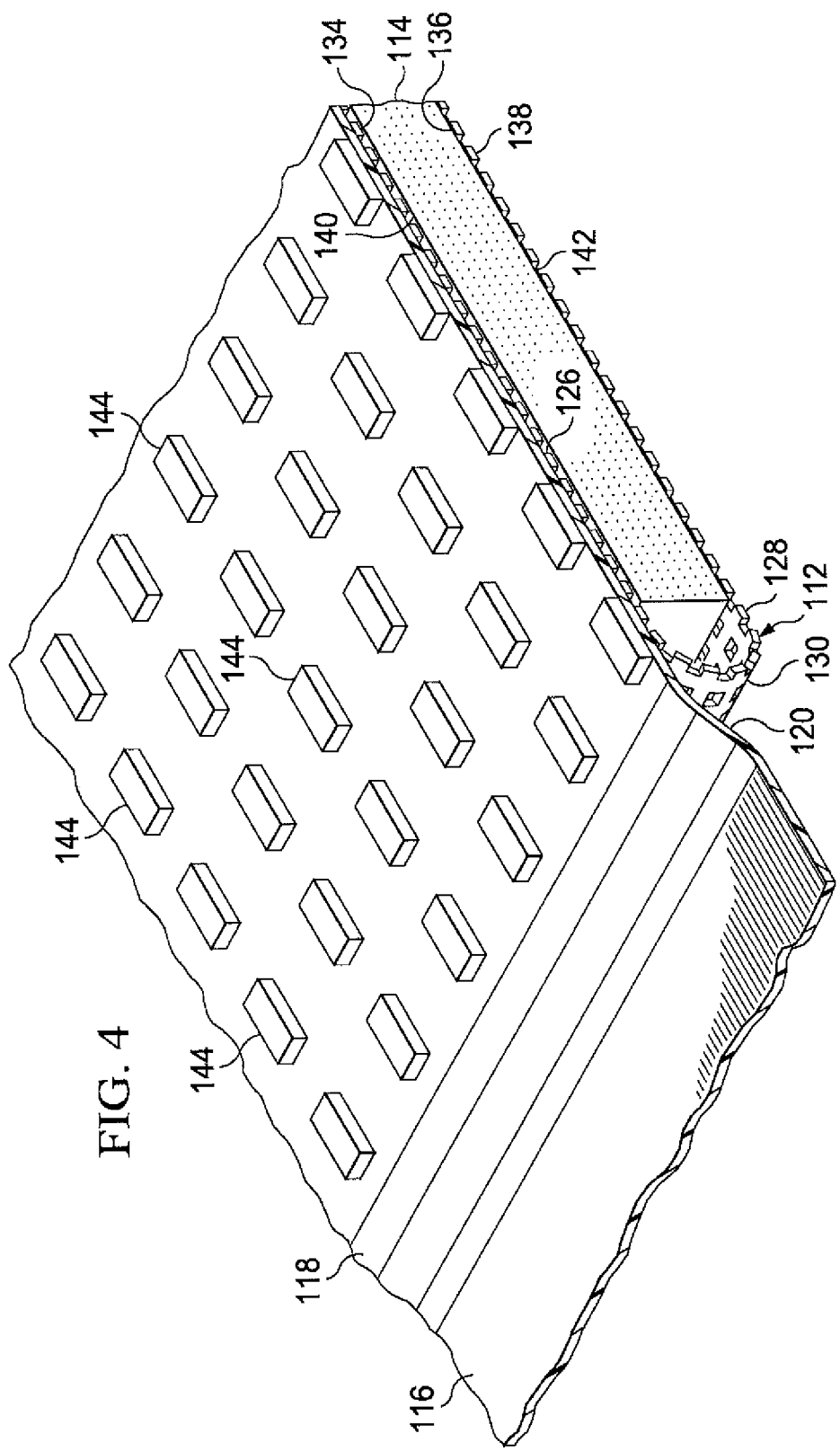
FIG. 4 is a perspective view, with a portion shown in cross section, of a portion of the wound dressing of FIG. 3.
Figure 5:
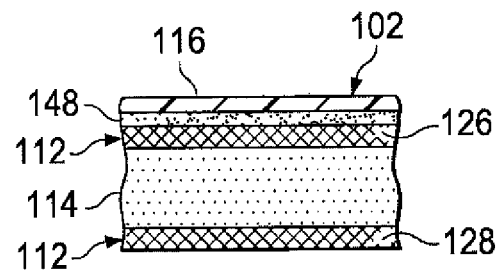
FIG. 5 is a cross section of an illustrative embodiment of a portion of a wound dressing including a filtering layer.
Figure 6:
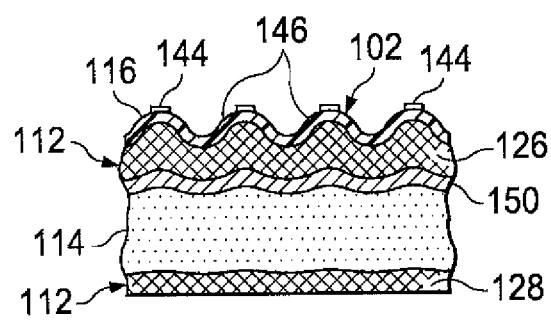
FIG. 6 is a cross section of an illustrative embodiment of a portion of a wound dressing including a hydro-activated, exothermic material.

With reference to FIGS. 4-6, a plurality of nano-antennas 144 or nantennas have been added on the first side 118 of the high-moisture-vapor-transmission-rate drape 116. The plurality of nano-antennas 144 are a way of harvesting the environmental energy, e.g., energy from light or heat from the patient. A nano-antenna is an electromagnetic collector designed to absorb specific wavelengths that are proportional to the size of the nano-antenna. The nano-atennas 144 may be sized to focus on absorbing infrared radiation with wavelengths from 1 micron to 300 microns and may, in some embodiments, focus on 12 micron wavelengths which are the wavelength that the human body at normal temperature emits as heat. Design of the nano-antenna 144 may be a type of interlocking spiral such as those from MicroContinuum Inc. These type of antennas are manufactured by photo-lithography using gold foil on a plastic sheet substrate. The energy harnessed is electrical.

Separate or in addition to the nano-antennas 144, the high-moisture-vapor-transmission-rate drape 116 may include corrugated portions 146 as shown in FIG. 6. The corrugated portions 146 increase the surface area available to assist with evaporation and may encourage turbulent air flow across the first side 118 of the high-moisture-vapor-transmission-rate drape 116.

Referring primarily to FIGS. 1-4, in operation, according to one illustrative embodiment, the thermally-conductive, vapor-permeable member 112, which has the liquid-processing member 114 between portions thereof, is disposed proximate to the wound 104. The patient-interface member 128 of the thermally-conductive, vapor-permeable member 112 is disposed proximate to the wound 104. The high-moisture-vapor-transmission-rate drape 116 is disposed over the thermally-conductive, vapor-permeable member 112. In particular, the second, patient-facing side 120 of the high-moisture-vapor-transmission-rate drape 116 is disposed proximate to the first side 132 of the drape-interface member 126.

Before applying the high-moisture-vapor-transmission-rate drape 116, if applicable, release liners (not shown) may be removed from the attachment device 124. The wound dressing 102 may remain on the wound 104 for a few hours up to many days, e.g., 2 days, 4 days, 7 days, or more. A saturation indicator (visual indicator of moisture) (not shown) may be added to the thermally-conductive, vapor-permeable member 112 or liquid-processing member 114 to indicate when the wound dressing 102 is full. If nano-antennas 144 are included (e.g., FIGS. 3-4, 6, 12), the nano-antennas 144 may absorb energy from ambient light or may receive light from a directed light source (see, e.g., FIG. 12).

The wound 104 produces a liquid, e.g., exudate, that flows through the patient-interface member 128 and into the liquid-processing member 114, which temporarily holds the liquid. The liquid in the liquid-processing member 114 that is against or near the high-moisture-vapor-transmission-rate drape 116 evaporates and is transmitted through the high-moisture-vapor-transmission-rate drape 116. The transmission rate through the high-moisture-vapor-transmission-rate drape 116 is increased or enhanced by the thermal energy delivery from the patient 106 through the thermally-conductive, vapor-permeable member 112. The transmission rate may further be enhanced by additional energy added externally or internally as presented elsewhere herein.

Referring now primarily to FIG. 5, a cross section of a portion of a wound dressing 102 is shown according to one illustrative embodiment. This embodiment is analogous to the embodiment of FIG. 1, except a filtering layer 148 has been added. The filtering layer 148 is shown disposed between the high-moisture-vapor-transmission-rate drape 116 and the drape-interface member 126 of the thermally-conductive, vapor-permeable member 112. It should be understood that the filtering layer 148 may be at any location between the patient and the high-moisture-vapor-transmission-rate drape 116. It should also be understood that filtering layer 148 may be used with any embodiment herein.

The filtering layer 148 may serve one or more purposes. The filtering layer 148 may prevent any substances other than water vapor from reaching the high-moisture-vapor-transmission-rate drape 116. In addition or separately, the filtering layer 148 may serve to filter odors from the vapor transmitted through the high-moisture-vapor-transmission-rate drape 116 to the atmosphere. The filtering layer may be formed from activated carbon material, activated clays (such as Bentonite), silicone resins, or coated porous (foams, sintered media) elements.

Referring primarily to FIG. 6, an illustrative embodiment of a portion of a wound dressing 102 is shown that is analogous to the wound dressing 102 of FIG. 1, except that the high-moisture-vapor-transmission-rate drape 116 includes corrugated portions 146 and nano-antennas 144 and the wound dressing 102 includes a hydro-activated, exothermic material 150. The corrugated portions 146 and nano-antennas 144 have previously been discussed. The hydro-activated, exothermic material 150 may be disposed on or in the liquid-processing member 114 near the drape-interface member 126. When the hydro-activated, exothermic material 150 is exposed to a watery liquid, a resultant chemical reaction produces heat. As one illustrative, non-limiting example, the hydro-activated, exothermic material 150 may be calcium oxide such that when water in the exudate reaches the hydro-activated, exothermic material 150 a reaction occurs: $CaO_{(s)}+H_2O_{(l)} \rightarrow Ca(OH)2_{(s)}$. Another example, albeit a highly exothermic (and more caustic) one, is $NaO_{(s)}+H_2O_{(l)} \rightarrow NaOH_{(s)}$. Another example (used in hand warmers for example) is $4Fe_{(s)}+3O_{2(g)} \rightarrow 2Fe_2O_{3(s)}$. This reaction is one way, but a reversible reaction may be used as well.

Figure 7:
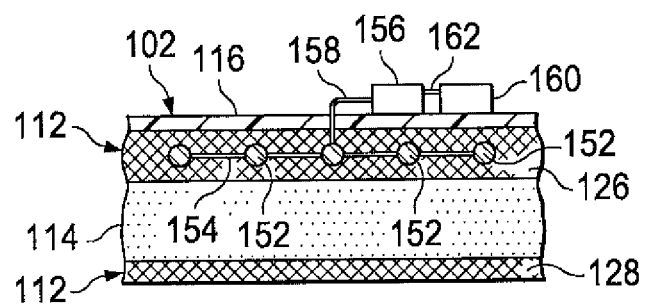
FIG. 7 is a cross section of an illustrative embodiment of a portion of a wound dressing including an electrical heating element.

Referring now primarily to FIG. 7, an illustrative embodiment of a portion of a wound dressing 102 that includes an internal heat source in the form of an electrical heating element 152 is presented. The wound dressing 102 is analogous in most respects to the wound dressing of FIG. 1, except that it further includes the electrical heating element 152 and associated components. The electrical heating element 152 may be a resistive heating element that is disposed inside or on the thermally-conductive, vapor-permeable member 112 and is thereby thermally coupled to the high-moisture-vapor-transmission-rate drape 116. The electrical heating element 152 provides thermal energy when energized.

The illustrative electrical heating element 152 is shown as a plurality of electrical conduits disposed within the thermally-conductive, vapor-permeable member 112 and electrically coupled to one another by leads 154. The electrical heating element 152 is electrically coupled to a control circuit 156 by another lead 158. A power supply 160 is electrically coupled to the control circuit 156 by another lead 162. The control circuit 156 may be used to set the desired temperature and to control the heat developed by the electrical heating element 152.

Figure 8:
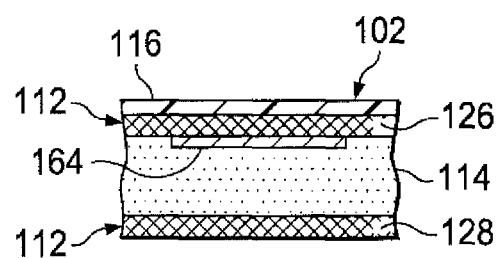
FIG. 8 is a cross section of an illustrative embodiment of a portion of a wound dressing.

Referring now primarily to FIG. 8, an illustrative embodiment of a portion of a wound dressing 102 that includes an internal heat source in the form of a piezoelectric member 164 is shown. The wound dressing 102 is analogous in most respects to the wound dressing of FIG. 1, except that the wound dressing 102 further includes the piezoelectric member 164. The piezoelectric member 164 is operable to provide energy to the wound dressing 102 when the piezoelectric member 164 is moved. The piezoelectric member 164 generates an electrical current during flexing that is then used to generate heat.

Figure 9:
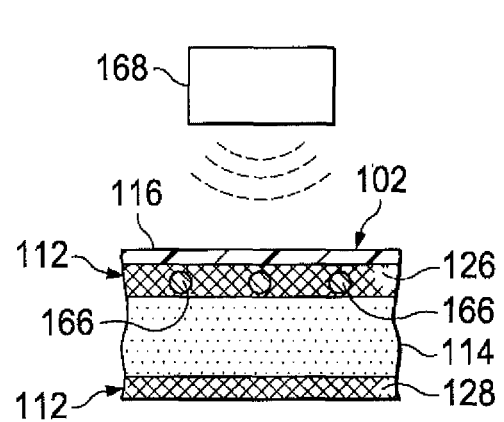
FIG. 9 is a cross section of an illustrative embodiment of a portion of a wound dressing including inductive elements.

Referring now primarily to FIG. 9, an illustrative embodiment of a portion of a wound dressing 102 that includes inductive elements 166 and a source of magnetic energy 168 is presented. The wound dressing 102 is analogous in most respects to the wound dressing of FIG. 1, except the inductive elements 166 have been added. The inductive elements 166 are disposed within or on the thermally-conductive, vapor-permeable member 112. The source of magnetic energy 168 emits magnetic energy that is received by the inductive elements 166 to produce thermal energy that is conducted to the thermally-conductive, vapor-permeable member 112 and thereby to the high-moisture-vapor-transmission-rate drape 116.

Figure 10:
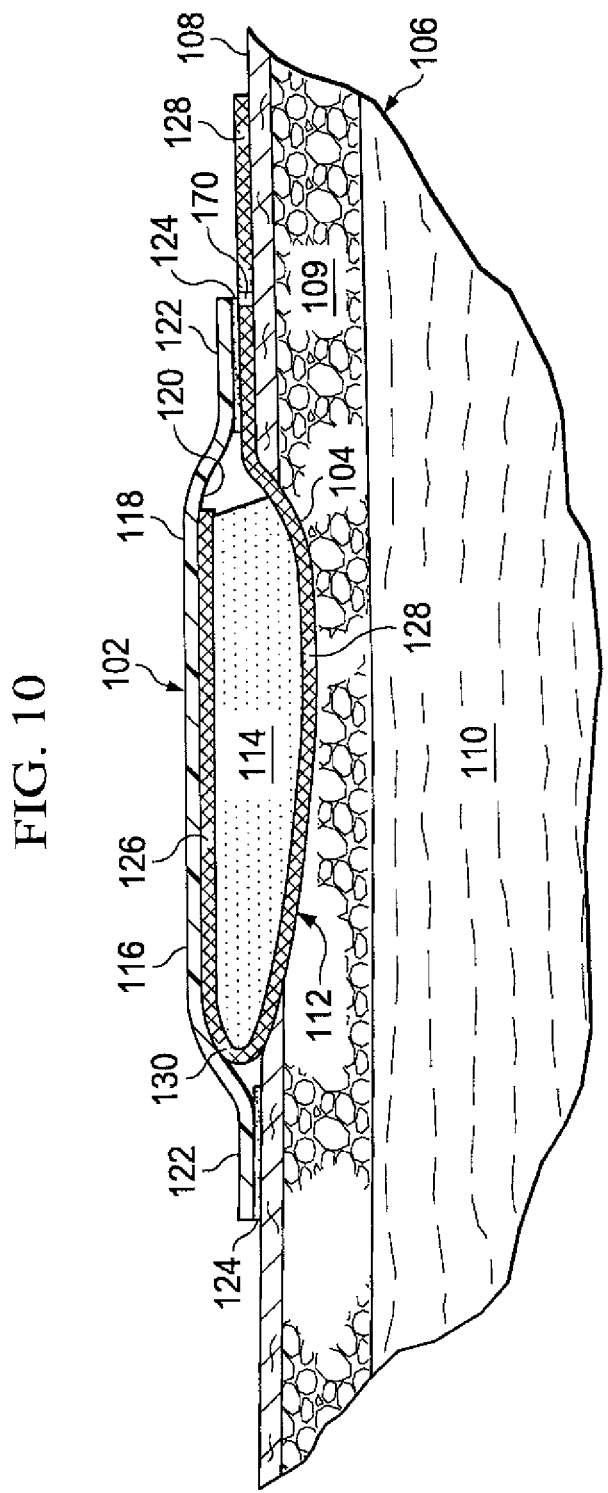
FIG. 10 is a cross section of an illustrative embodiment of a wound dressing shown on a patient.
Figure 11:
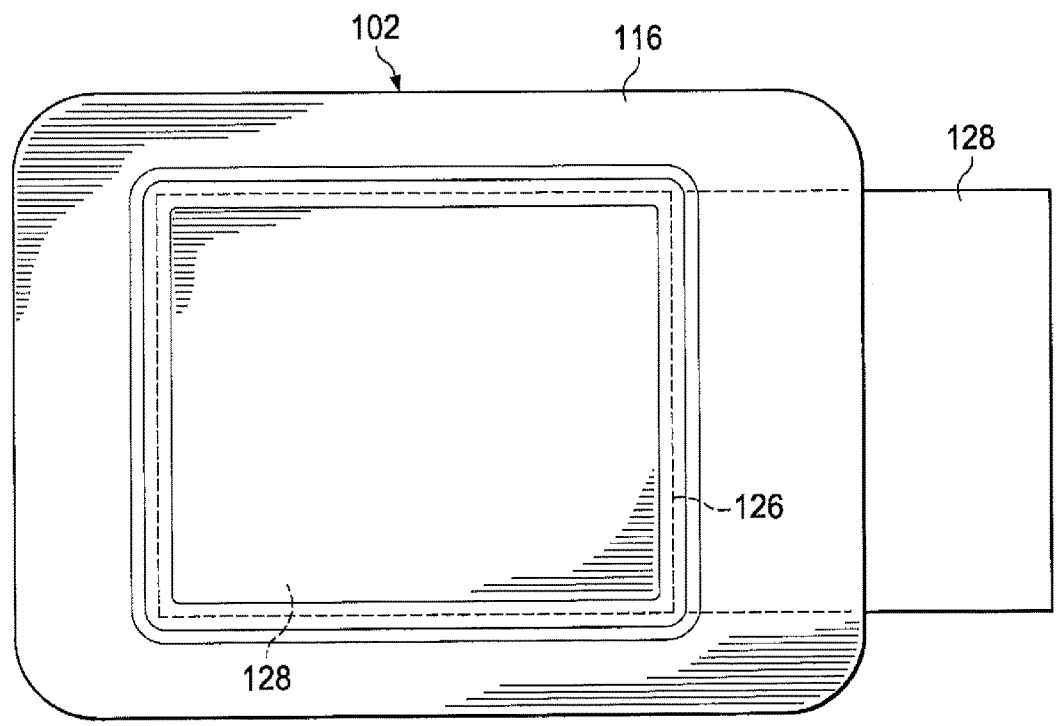
FIG. 11 is a plan view of the illustrative embodiment of a wound dressing of FIG. 10.

Referring now primarily to FIGS. 10 and 11, an illustrative embodiment of a wound dressing 102 is presented that is analogous in most respects to the wound dressing 102 of FIG. 1, except that the wound dressing 102 includes a patient-interface member 128 that is larger than the drape-interface member 126 of the thermally-conductive, vapor-permeable member 112. The patient-interface member 128 is larger to provide a greater surface area over which to capture heat from the patient. A seal 170 may be provided on a portion of the patient-interface member 128 proximate to an edge of the drape-interface member 126 to provide a fluid seal. The seal inhibits fluid flow but allows thermal energy to pass. Thus, in this illustrative embodiment, the planar surface area ($A_1$) of the drape-interface member 126 is less than the planar surface area ($A_2$) of the patient-interface member 128, i.e., $A_1 < A_2$. An adhesive (not shown) may be applied on peripheral portion of the patient-facing side of the patient-interface member 128 to hold the additional portion of the patient-interface member 128 to intact skin on the patient.

Referring to FIGS. 5-11, in operation, according to another illustrative embodiment, the wound dressing 102 is disposed proximate to the wound 104. The patient-interface member 128 is proximate to the wound 104. The other layers or members are assembled or pre-assembled as shown in the figures with the high-moisture-vapor-transmission-rate Drape on the top (for the orientation shown).

Referring now primarily to FIG. 5, in operation, the vapor leaving the thermally-conductive, vapor-permeable member 112 moves through the filtering layer 148, which removes odor or particulates that might otherwise escape. Referring primarily to FIG. 6, the vapor transmission rate is enhanced by the patient's body heat and heat from the hydro-activated, exothermic material 150 once the watery liquid reaches the hydro-activated, exothermic material 150. For embodiments including the nano-antennas 144 (e.g., FIGS. 3, 4, 6), additional energy is added thereby. Moreover, for the embodiment shown in FIG. 6, the transmission rate may be relatively increased by using a greater surface area due to the corrugated portions 146.

Referring primarily to FIG. 7, in operation according to one illustrative embodiment; the transmission rate is enhanced by the patient's body heat and heat from the electrical heating element 152. The amount of heat added by the electrical heating element 152 is controlled by the control circuit or controller 156. An electrical fill indicator (not shown) may be included in the liquid-processing member 114 and electrically coupled to the control circuit 156 such that the control circuit 156 activates the electrical heating element 152 once the liquid-processing member 114 is saturated. Alternatively, the control circuit 156 may activate the electrical heating element 152 based on timer intervals or when manually activated.

Referring primarily to FIG. 8, in operation according to one illustrative embodiment, the transmission rate is enhanced by the patient's body heat and heat from the piezoelectric member 164. The piezoelectric member 164 may take movement and create thermal energy. In another illustrative embodiment, the element labeled 164 may be a material that otherwise generates heat as the element is flexed. For example, without limitation, the following may be used: castable polyester polyurethane elastomers based on the system polycaprolactone dial (Capa 225)/trans 1.4-cyclohexane diisocyanate (CHDI)/1.4-butane diol (1,4-BD) and 1.4-cyclohexane dimethanol (1,4-CHDM). Referring now primarily to FIG. 9, the transmission rate is enhanced by the patient's body heat and heat from the inductive elements 166 that are activated by the source of magnetic energy 168.

Figure 12:
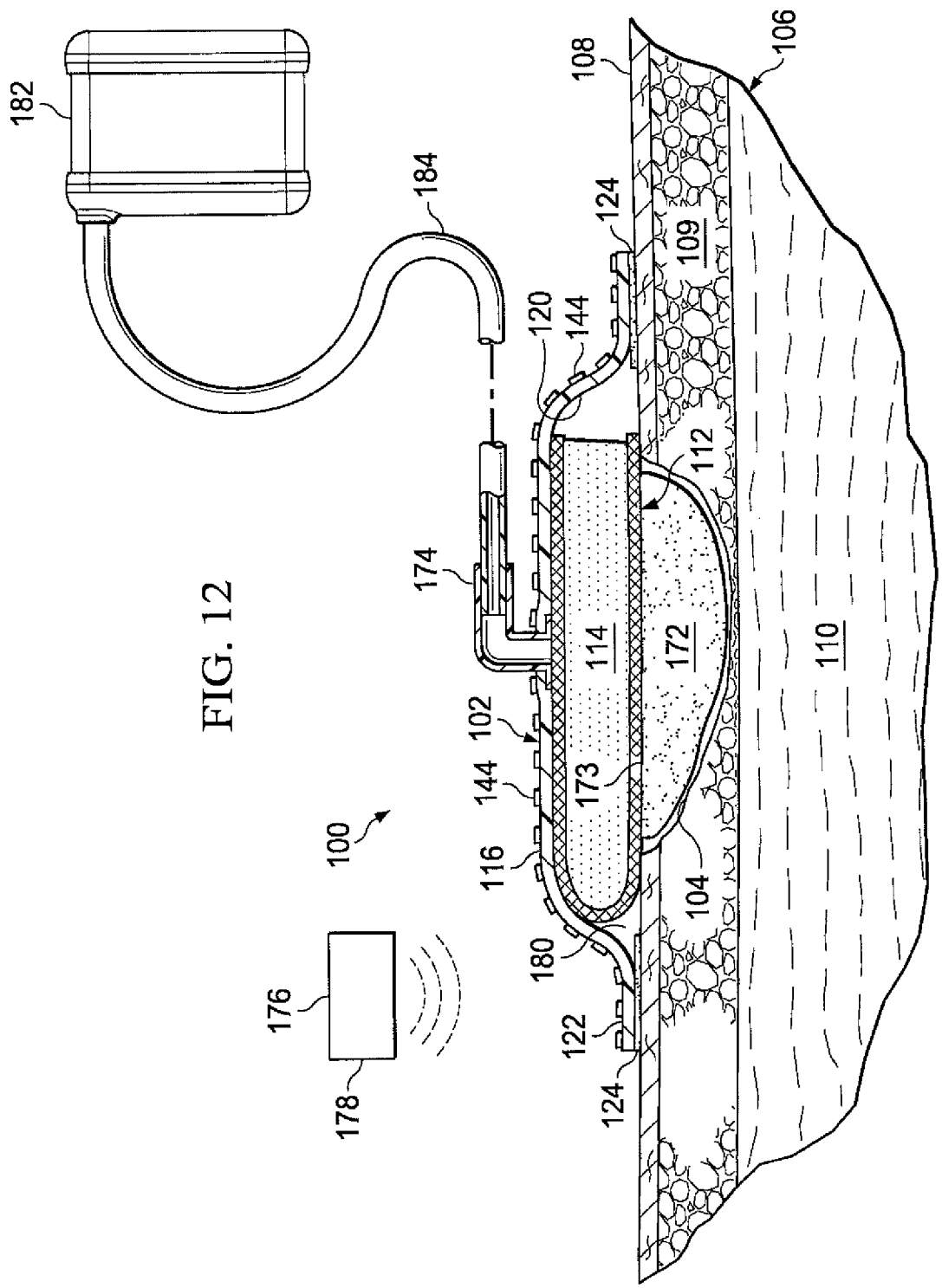
FIG. 12 is a cross section of an illustrative system for treating a wound.

Referring now primarily to FIG. 12, an illustrative system 100 for treating a wound 104 on a patient 106 is presented. The system 100 includes a wound dressing 102, which is analogous in many respects to the wound dressing 102 of FIG. 1. The system 100 provides for enhanced liquid management and also for the application of reduced pressure on a wound 104.

The system 100 includes a manifold member 172 disposed proximate to the wound 104. In this illustrative example, the wound 104 extends through epidermis 108, dermis 109, and into subcutaneous tissue 110. The manifold member 172 is a substance or structure that is provided to assist in applying reduced pressure to, delivering fluids to, or removing fluids from a tissue site or wound 104. The manifold member 172 includes a plurality of flow channels or pathways that distribute fluids provided to and removed from the tissue site around the manifold member 172. In one illustrative embodiment, the flow channels or pathways are interconnected to improve distribution of fluids provided to or removed from the wound 104. The manifold member 172 may be a biocompatible material that is capable of being placed in contact with the wound 104 and distributing reduced pressure. Examples of manifold members 172 include, without limitation, one or more of the following: devices that have structural elements arranged to form flow channels, such as, for example, cellular foam, open-cell foam, porous tissue collections, liquids, gels, and foams that include, or cure to include, flow channels; porous material porous, such as foam, gauze, felted mat, or any other material suited to a particular biological application; or porous foam that includes a plurality of interconnected cells or pores that act as flow channels, e.g., a polyurethane, open-cell, reticulated foam such as GranuFoam® material manufactured by Kinetic Concepts, Incorporated of San Antonio, Tex.; a bioresorbable material; or a scaffold material.

In some situations, the manifold member 172 may also be used to distribute fluids such as medications, antibacterials, growth factors, and various solutions to the tissue site. Other layers may be included in or on the manifold member 172, such as absorptive materials, wicking materials, hydrophobic materials, and hydrophilic materials. In one illustrative, non-limiting embodiment, the manifold member 172 may be constructed from a bioresorbable material that remains in a patient's body following use of the reduced-pressure dressing. Suitable bioresorbable materials include, without limitation, a polymeric blend of polylactic acid (PLA) and polyglycolic acid (PGA). The polymeric blend may also include without limitation polycarbonates, polyfumarates, and capralactones.

The manifold member 172 may further serve as a scaffold for new cell-growth, or a scaffold material may be used in conjunction with the manifold member 172 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials.

As with other embodiments herein, the wound dressing 102 includes a high-moisture-vapor-transmission-rate drape 116; a thermally-conductive, vapor-permeable member 112; and a liquid-processing member 114. The high-moisture-vapor-transmission-rate drape 116 may include nano-antennas 144. Applied on or through the high-moisture-vapor-transmission-rate drape 116 is a reduced-pressure interface 174. In one illustrative embodiment, the reduced-pressure interface 174 is a T.R.A.C.® Pad or Sensa T.R.A.C.® Pad available from KCI of San Antonio, Tex.

An external energy source 176 may be used to provide additional energy to the wound dressing 102. For example, the external energy source 176 may be a light source 178, e.g., an LED light, that provides light to the high-moisture-vapor-transmission-rate drape 116 directly or by providing energy to the nano-antennas 144.

The high-moisture-vapor-transmission-rate drape 116 creates a sealed space 180 between the wound 104 and the second, patient-facing side 120 of the high-moisture-vapor-transmission-rate drape 116. A reduced-pressure source 182 is fluidly coupled to the sealed space 180. The reduced-pressure source 182 may be any device for supplying a reduced pressure, such as a vacuum pump, wall suction, micro-pump, or other source. While the amount and nature of reduced pressure applied to a tissue site will typically vary according to the application, the reduced pressure will typically be between −5 mm Hg (−667 Pa) and −500 mm Hg (−66.7 kPa) and more typically between −75 mm Hg (−9.9 kPa) and −300 mm Hg (−39.9 kPa).

The reduced-pressure source 182 may be fluidly coupled to the sealed space 180, which includes the manifold member 172, by a reduced-pressure delivery conduit 184 and the reduced-pressure interface 174 or by directly inserting the reduced-pressure delivery conduit 184 through the high-moisture-vapor-transmission-rate drape 116 into the sealed space 180. In addition, the fluid coupling may be due to the position of the reduced-pressure source 182; for example, if the reduced-pressure source 182 is a micro-pump, the intake may be directly, fluidly coupled to the sealed space 180. In addition, in the latter example, the micro-pump is thermally coupled to the high-moisture-vapor-transmission-rate drape 116.

In operation, according to one illustrative embodiment, the manifold member 172 is disposed proximate to the wound 104. The wound dressing 102 is placed proximate to a first side 173 of the manifold member 172. The high-moisture-vapor-transmission-rate drape 116 over the patient's skin creates the sealed space 180. Using the reduced-pressure interface 174 or otherwise, the reduced-pressure delivery conduit 184 is fluidly coupled to the sealed space 180 and thereby the manifold member 172. Reduced pressure is then applied to help treat the wound 102. In the embodiment shown, liquids are delivered to the reduced-pressure source 182, but evaporation and transmission through the high-moisture-vapor-transmission-rate drape 116 may also occur. For embodiments in which the reduced-pressure source 182 is a micro-pump, the liquid will be retained in the wound dressing 102 until transmitted through the high-moisture-vapor-transmission-rate drape 116. The transmission rate is enhanced by the patient's body heat (delivered through the thermally-conductive, vapor-permeable member 112) and may be enhanced by nano-antennas 144 if included. The nano-antennas 144 may be energized by a light source 178.

Figure 13:
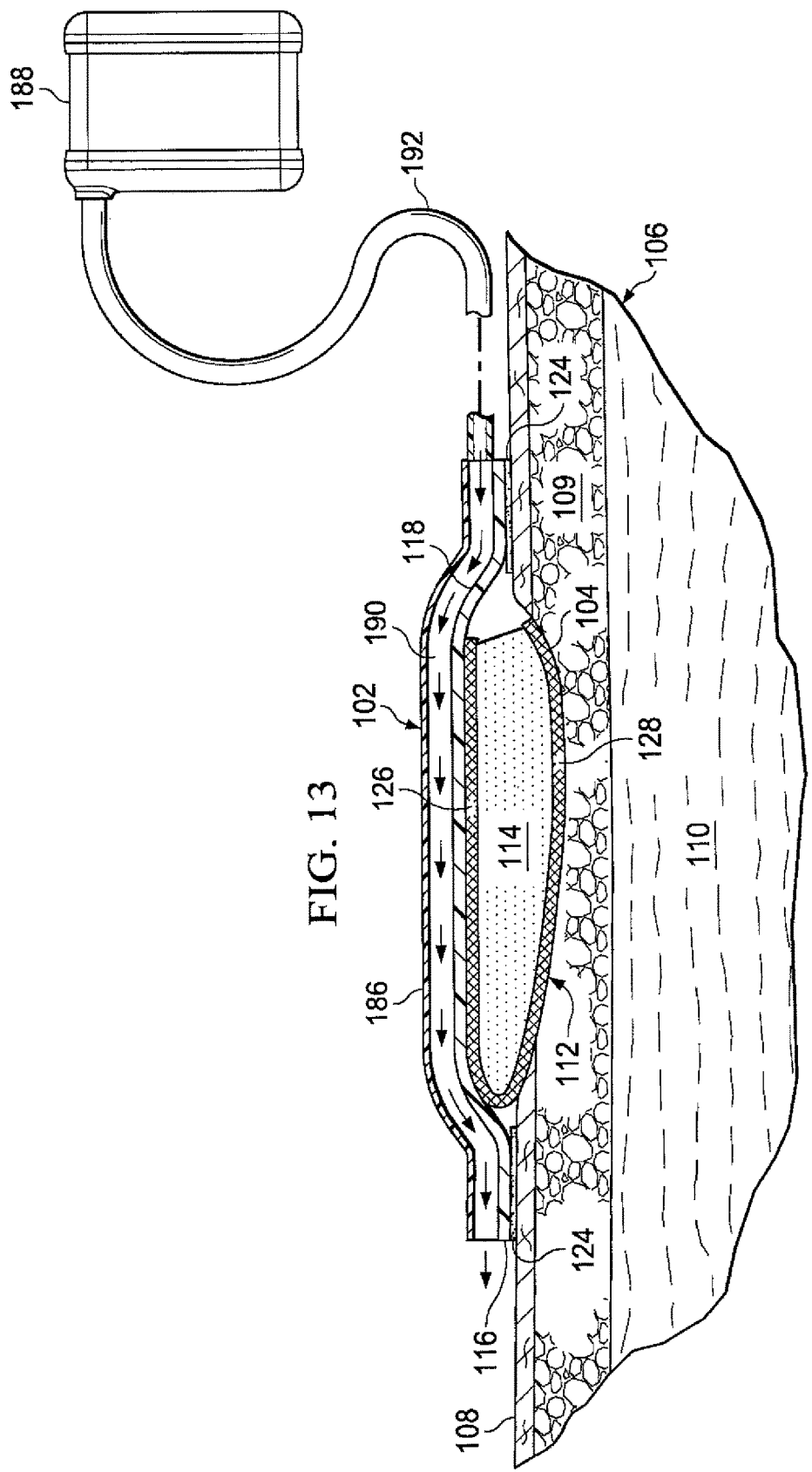
FIG. 13 is a cross section of an illustrative system for treating a wound.

Referring now primarily to FIG. 13, another illustrative embodiment of a wound dressing 102 is presented. The wound dressing 102 is analogous in most respects to the wound dressing 102 of FIG. 1, except external baffles 186 and an air mover 188 have been added. The external baffles 186 are on the first side of the high-moisture-vapor-transmission-rate drape 116 and form a channel 190. The air mover 188 is fluidly coupled to the channel 190 by a conduit 192. The air mover 188 provides air flow against the first side 118 of the high-moisture-vapor-transmission-rate drape 116 and thereby further increases the evaporation rate. The components of the various figures may be combined with others. Thus, for example, the air mover 188 and external baffles 186 may be added to any of the other embodiments herein.

Figure 14:
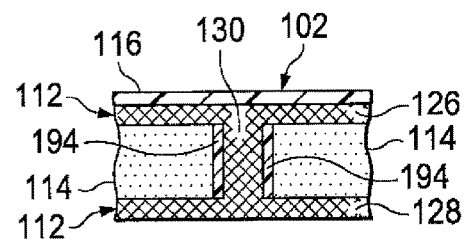
FIG. 14 is a cross section of an illustrative embodiment of a portion of a wound dressing.

Referring now to FIG. 14, another illustrative embodiment of a portion of a wound dressing 102 is presented. The wound dressing 102 is analogous in most respects to the wound dressing 102 of FIG. 1. The wound dressing 102 has a thermally-conductive, vapor-permeable member 112. A liquid-processing member 114 is between portions of the thermally-conductive, vapor-permeable member 112. The wound dressing 102 further includes a high-moisture-vapor-transmission-rate drape 116. The thermally-conductive, vapor-permeable member 112 has a drape-interface member 126, a patient-interface member 128, and a coupling member 130. In this embodiment, the coupling member 130 is presented in a different location in part to emphasize that the coupling member 130 may be in numerous locations.

In the embodiments presented previously, the coupling member 130 has been to one side of the liquid-processing member 114. In the illustrative embodiment of the present embodiment, the coupling member 130 extends from the patient-interface member 128 to the drape-interface member 126 through the body or main portion of the liquid-processing member 114. Because it is generally desirable to transfer heat from the patient to the drape-interface member 126 without heating up the liquid-processing member 114, insulation 194 may be placed around the coupling member 130. It should be understood that the coupling member 130 functions to thermally couple the drape-interface member 126 and the patient-interface member 128 and may be located at any point with respect to those members, e.g., sides or middle or any where between.

Although the present invention and its advantages have been disclosed in the context of certain illustrative, non-limiting embodiments, it should be understood that various changes, substitutions, permutations, and alterations can be made without departing from the scope of the invention as defined by the appended claims. It will be appreciated that any feature that is described in connection to any one embodiment may also be applicable to any other embodiment. For example, without limitation, the nano-antennas 144 may be added to any embodiment herein. As another example, without limitation, the filtering layer 148 may be added to any embodiment herein. As another example, without limitation, the corrugated portions 146 may be added to any of the embodiments herein.

As another example, without limitation, the hydro-activated, exothermic material 150 may be added to any of the embodiments herein. As still another example the electrical heating element 152 (and associated components) may be added to any embodiment herein or the piezoelectric member 164 added to any embodiment. As still another example, without limitation, reduced pressure (see FIG. 12) may be used with any of the embodiments. As one more example, without limitation, the external baffles 186 and air mover 188 (FIG. 13) may be used with any embodiment. Moreover, the different components may be used in any combination.

Thus, for example, without limitation, a wound dressing 102 may have a nano-antennas 144 on the high-moisture-vapor-transmission-rate drape 116, a filtering layer 148 below (for orientation shown in FIG. 5), a hydro-activated, exothermic material 150 proximate the filtering layer 148, and an electrical heating element 152 in the thermally-conductive, vapor-permeable member 112. Numerous other examples are possible. Finally, while the illustrative embodiments have been shown using body heat directed by the thermally-conductive, vapor-permeable member 112, it should be appreciated that some of the embodiments may forgo such a component and use other heating elements alone, e.g., the hydro-activated, exothermic material 150; electrical heating element 152; or piezoelectric member 164.

According to another illustrative embodiment, the piezoelectric member 164 (FIG. 8) may be included with the reduced-pressure components of FIG. 12. Then in operation, the reduced-pressure components may be used in a pulsed fashion to move and excite the piezoelectric member 164 to generate heat.

The illustrative embodiments herein may provide numerous perceived advantages for healthcare providers and patients. A number of possible examples follow. For example, the wound dressing 102 may have an enhanced capacity because the wound dressing 102 is able to offload liquid from the wound dressing 102 in the form of vapor exiting the wound dressing 102 through the high-moisture-vapor-transmission-rate drape 116. And, because of the additional thermal energy, the wound dressings 102 are operable to transmit relatively more liquid through the high-moisture-vapor-transmission-rate drape 116 over a given time. Moreover, the wound dressings 102 may stay in place longer. The wound dressings 102 may be used without requiring additional training. The wound dressings 102 may convert liquids retained into the wound dressing 102 to a gel and thereby make disposal easier.

It will be understood that the benefits and advantages described above may relate to one embodiment or may relate to several embodiments. It will further be understood that reference to "an" item refers to one or more of those items.

The steps of the methods described herein may be carried out in any suitable order, or simultaneously where appropriate.

Where appropriate, aspects of any of the embodiments described above may be combined with aspects of any of the other embodiments described to form further examples having comparable or different properties and addressing the same or different problems.

It will be understood that the above description of preferred embodiments is given by way of example only and that various modifications may be made by those skilled in the art. The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the scope of the claims.

We claim:

1. A dressing comprising:
a first interface comprising a first thermally-conductive, vapor-permeable material, the first interface configured to be disposed adjacent a tissue site;
a second interface coupled to the first interface and comprising a second thermally-conductive, vapor-permeable material;
a processor disposed between the first interface and the second interface, the processor configured to temporarily store liquid and release vapor to the second interface; and
a drape configured to be disposed over the first interface and the second interface, a surface of the drape further configured to contact and be fluidly coupled to a surface of the second interface opposite the processor;
whereby the first interface is configured to harvest thermal energy from the tissue site, the second interface is configured to receive the thermal energy from the tissue site, and the harvested thermal energy is configured to increase evaporation of liquid from the processor through the drape.

2. The dressing of claim 1, wherein:
the first interface has a first end and a second end;
the second interface has a first end and a second end; and
the first end of the first interface is coupled to the first end of the second interface.

3. The dressing of claim 2, further comprising a third interface, the third interface coupling the first end of the first interface to the first end of the second interface.

4. The dressing of claim 3, wherein the third interface comprises a first end, a second end, and an elbow extending between the first end and the second end, the elbow providing a 180 degree turn between the first end and the second end.

5. The dressing of claim 1, wherein:
the first interface has a first end, a second end, and a center between the first end and the second end;

the second interface has a first end, a second end, and a center between the first end and the second end; and the center of the first interface is coupled to the center of the second interface.

6. The dressing of claim 5, further comprising a column having a first end coupled to a surface of the first interface facing the processor and a second end coupled to a surface of the second interface facing the processor.

7. The dressing of claim 5, wherein the second interface is coupled to the first interface through the processor.

8. The dressing of claim 5, wherein the center of the first interface is equidistant between the first end and the second end.

9. The dressing of claim 5, wherein the center of the second interface is equidistant between the first end and the second end.

10. The dressing of claim 1, wherein the first interface and the second interface comprise one or more of: an active carbon material, metallic fiber, zinc oxide, and silver.

11. The dressing of claim 1, wherein the processor comprises at least one of: a foam, a non-woven, a super absorbent material, and a gel material.

12. The dressing of claim 1, further comprising a filter layer disposed between the processor and at least one of the first interface and the second interface.

13. The dressing of claim 1, wherein the drape includes a first side facing the second interface and further comprising nano-antennae coupled to a second side of the drape, the nano-antennae configured to receive external energy.

14. The dressing of claim 1, wherein the drape is at least partially corrugated.

15. The dressing of claim 1, wherein the processor comprises a hydro-activated, exothermic material that reacts with wound exudate to generate heat.

16. The dressing of claim 1, wherein the processor comprises a calcium oxide configured to exothermically react with wound exudate to generate heat.

17. The dressing of claim 1, further comprising:
a heating element coupled to the drape;
a power supply electrically coupled to the heating element; and
a control circuit coupled to the power supply.

18. The dressing of claim 1, further comprising a piezoelectric member that is operable to provide thermal energy when moved, wherein the piezoelectric member is thermally coupled to the drape.

19. The dressing of claim 1, further comprising a motion-activated heating element coupled to the drape.

20. The dressing of claim 1, further comprising an external heater configured to transmit heat to the drape.

21. The dressing of claim 1, further comprising baffles on a first side of the drape and an air mover configured to deliver air flow across the baffles.

22. A dressing comprising:
a first interface configured to be disposed adjacent a tissue site, the first interface being fluid permeable and further configured to harvest thermal energy from the tissue site;
a processor disposed adjacent to the first interface, the processor configured to receive and store liquid;
a second interface disposed adjacent to the processor and coupled to the first interface to receive the thermal energy harvested from the tissue site, the second interface being fluid permeable; and
a drape configured to be disposed over the second interface so that a surface of the second interface opposite the processor contacts a surface of the drape, wherein the drape includes a first side facing the second interface and further comprising nano-antennae coupled to a second side of the drape, the nano-antennae configured to receive external energy.

23. A dressing comprising:
a first interface configured to be disposed adjacent a tissue site, the first interface being fluid permeable and further configured to harvest thermal energy from the tissue site;
a processor disposed adjacent to the first interface, the processor comprising a calcium oxide configured to exothermically react with wound exudate to generate heat and wherein the processor is configured to receive and store liquid;
a second interface disposed adjacent to the processor and coupled to the first interface to receive the thermal energy harvested from the tissue site, the second interface being fluid permeable; and
a drape configured to be disposed over the second interface so that a surface of the second interface opposite the processor contacts a surface of the drape.

24. A dressing comprising:
a first interface configured to be disposed adjacent a tissue site, the first interface being fluid permeable and further configured to harvest thermal energy from the tissue site;
a processor disposed adjacent to the first interface, the processor configured to receive and store liquid;
a second interface disposed adjacent to the processor and coupled to the first interface to receive the thermal energy harvested from the tissue site, the second interface being fluid permeable;
a drape configured to be disposed over the second interface so that a surface of the second interface opposite the processor contacts a surface of the drape; and
a piezoelectric member that is operable to provide thermal energy when moved, wherein the piezoelectric member is thermally coupled to the drape.

25. A dressing comprising:
a first interface configured to be disposed adjacent a tissue site, the first interface being fluid permeable and further configured to harvest thermal energy from the tissue site;
a processor disposed adjacent to the first interface, the processor configured to receive and store liquid;
a second interface disposed adjacent to the processor and coupled to the first interface to receive the thermal energy harvested from the tissue site, the second interface being fluid permeable;
a drape configured to be disposed over the second interface so that a surface of the second interface opposite the processor contacts a surface of the drape; and
a motion-activated heating element coupled to the drape.

26. A dressing comprising:
a first interface configured to be disposed adjacent a tissue site, the first interface being fluid permeable and further configured to harvest thermal energy from the tissue site;
a processor disposed adjacent to the first interface, the processor configured to receive and store liquid;
a second interface disposed adjacent to the processor and coupled to the first interface to receive the thermal energy harvested from the tissue site, the second interface being fluid permeable;
a drape configured to be disposed over the second interface so that a surface of the second interface opposite the processor contacts a surface of the drape;

one or more baffles on a first side of the drape; and an air mover configured to deliver air flow across the baffles.

27. A dressing comprising:

a first interface configured to be disposed adjacent a tissue site, the first interface being fluid permeable and further configured to harvest thermal energy from the tissue site, the first interface having a first end and a second end;

a processor disposed adjacent to the first interface, the processor configured to receive and temporarily store liquid;

a second interface disposed adjacent to the processor and coupled to the first interface to receive the thermal energy harvested from the tissue site, the second interface being fluid permeable and having a first end and a second end;

a third interface coupling the first end of the first interface to the first end of the second interface, wherein the third interface comprises a first end, a second end, and an elbow extending between the first end of the third interface and the second end of the third interface, the elbow providing a 180 degree turn between the first end of the third interface and the second end of the third interface; and a drape configured to be disposed over the second interface so that a surface of the second interface opposite the processor contacts a surface of the drape;

wherein the harvested thermal energy is configured to increase evaporation of liquid from the processor through the drape.

28. The dressing of claim 27, wherein the first interface and the second interface comprise one or more of: an active carbon material, metallic fiber, zinc oxide, and silver.

29. The dressing of claim 27, wherein the processor comprises at least one of: a foam, a non-woven, a super absorbent material, and a gel material.

30. The dressing of claim 27, further comprising a filter layer disposed between the processor and at least one of the first interface and the second interface.

31. The dressing of claim 27, wherein the drape is at least partially corrugated.

32. The dressing of claim 27, wherein the processor comprises a hydro-activated, exothermic material that reacts with wound exudate to generate heat.

33. The dressing of claim 27, wherein the processor comprises a calcium oxide configured to exothermically react with wound exudate to generate heat.

34. The dressing of claim 27, further comprising:

a heating element coupled to the drape;

a power supply electrically coupled to the heating element; and a control circuit coupled to the power supply.

35. The dressing of claim 27, further comprising an external heater configured to transmit heat to the drape.

* * * * *